United States Patent [19]

Ohnishi et al.

[11] Patent Number: 5,335,551
[45] Date of Patent: Aug. 9, 1994

[54] PILLOW TYPE PRESSURE DETECTOR

[75] Inventors: Michikazu Ohnishi, Hyogo; Hiroshi Ogoshi, Shiga; Kazuoki Takikawa, Hyogo, all of Japan

[73] Assignee: Kanegafuchi Kagaku Kogyo Kabushiki Kaisha, Osaka, Japan

[21] Appl. No.: 973,397

[22] Filed: Nov. 12, 1992

[51] Int. Cl.⁵ .................. G01L 7/08; G01L 9/00
[52] U.S. Cl. .......................... 73/731; 73/756; 128/672; 338/4
[58] Field of Search .......... 73/730, 731, 756, 727; 338/4; 128/672, 675

[56] References Cited

U.S. PATENT DOCUMENTS

| | | | |
|---|---|---|---|
| 4,227,420 | 10/1980 | Lamadrid | 73/730 |
| 4,309,993 | 1/1982 | Brown | 128/214 E |
| 4,541,284 | 9/1985 | Guagliumi et al. | 73/730 |
| 4,646,563 | 3/1987 | Jones | 73/730 |

FOREIGN PATENT DOCUMENTS 0132047  1/1985 European Pat. Off.
3838689  6/1990 Fed. Rep. of Germany.

OTHER PUBLICATIONS

EP-A-0 132 047 (Extracorporeal Medical Specialities), pp. 7-8.
Section Ch, Week 9302, Derwent Publications Ltd., London GB; Class J04, AN 93-015561 & JP-A-4 346 044 (Kaneka) 1 Dec. 1992 *abstract*.

*Primary Examiner*—Donald Woodiel
*Attorney, Agent, or Firm*—Armstrong, Westerman, Hattori, McLeland & Naughton

[57] ABSTRACT

A pillow type pressure detector having a base board on the front surface of which a load cell type load sensor is mounted; a holder cover which is so provided as to be spaced a predetermined distance from the base board; a flat-plate-shaped load transmitting board and a flat-plate-shaped retaining board positioned between the base board and the holder cover; a pillow type pressure reaction jig positioned between the load transmitting board and the retaining board; and a pillow holding member for clamping predetermined portions of the pressure reaction jig mounted over the base board and the holder cover. There are provided a mechanism for simultaneously swinging the load transmitting board and the retaining board relative to the base board, a mechanism elastically supporting the pillow holding member on the side of the base board and/or a thin-plate-shaped depressing member provided over the surface of the load sensor for fixedly secure the load sensor to the base. Distortion resulting from setting of the pressure detecting element is eliminated and accuracy of detection is improved.

4 Claims, 8 Drawing Sheets

PILLOW TYPE PRESSURE DETECTOR

BACKGROUND OF THE INVENTION

This invention relates to a pressure detector employed for a medical instrument, such as, a blood processing apparatus for detecting pressures linearly with a pillow type pressure reaction jig.

With a medical instrument, such as, a blood processing apparatus, blood ingredients, such as, corpuscles (blood cells) and plasma taken out of the body, are processed to remove unwanted materials therefrom and are then returned into the body. In other words, the blood is directly taken out of the patient's body, processed and then returned to such body. Therefore, it is essential that the use of the medical instrument will not adversely affect the patient's body. For this purpose, it is necessary to control the blood collection pressure, the plasma pressure, or plasma filtration pressure during blood processing, and the reinfusion or transfusion pressure into the body in such a manner that such pressures are in predetermined, allowable, ranges.

A conventional blood processing apparatus is shown in FIG. 12. In such apparatus, the blood collected, with a blood pump 2, is supplied to a blood filter 3, where such blood is divided into a corpuscle ingredient, and plasma. The plasma is delivered to a plasma filter 5, by a plasma pump 4, where such plasma is filtered to remove unwanted macromolecular ingredients. The condensed plasma is discharged by a plasma discharging pump 6. In this case, a replacing solution 7, corresponding in quantity to the condensed plasma discharged by the plasma discharging pump 6, is supplied with a replacing solution pump 8. The plasma thus processed is mixed with the corpuscle ingredient previously separated. The mixture of the plasma and the corpuscle component is returned into the body through a bubble detector 9.

The blood processing apparatus 1 has five pressure detectors in the above-described blood processing path; a blood collection pressure detector 10, a blood filtration pressure gauge 11, a plasma pressure gauge 12, a plasma filtration pressure gauge 13, and a reinfusion pressure gauge 14, all for detection of the presence or absence of abnormal conditions. These pressure detectors employ a drip chamber 15 as shown in FIG. 13. The drip chamber 15 has an air chamber 16, in its upper portion, communicated, through a pressure leading tube 17, to a pressure sensor 18 of strain gauge type. The pressure leading tube 17 is extended through a filter 19 which permits the flow of air but not of liquid. The air chamber 16 is further connected to a liquid inlet pipe 20 and an air vent pipe 21. The lower end portion of air chamber 16 is connected to a liquid outlet pipe 22. The air vent pipe 21 is for determining the level of liquid in drip chamber 15, and is normally closed.

The pressure in the air chamber 16 of the drip chamber 15 is detected with pressure sensor 18. In other words, in the conventional blood processing apparatus 1, pressure detectors, using the above-described drip chambers 15, are employed to detect a blood collection pressure, blood filtration pressure, plasma pressure, plasma filtration pressure, and reinfusion pressure.

In such conventional pressure detector, using the above-described drip chamber 15, the level of the liquid in the drip chamber 15 changes with the pressure. In order to absorb this change, it is necessary for the chamber to have a volume larger than a certain value. That is, the pressure detector is disadvantageous in that it unavoidably increases the priming volume. Furthermore, in order to operate the blood processing apparatus 1, it is essential to adjust the air vent pipe 21 and, thereby, adjust the level of liquid in drip chamber. That is, it is necessary to set the level of the liquid to the middle of the allowable range in which the level of the liquid in the drip chamber 15 is variable.

In the conventional blood processing apparatus 1, it is necessary to set the level of the liquid in each of the drip chambers 15. Some of the apparatus have three to eight drip chambers. In this case, it is rather troublesome to adjust all of those drip chambers. In addition, such setting of the level of the liquid in the drip chamber can be achieved only by a skilled person. This is one of the factors which lengthen the time required for the preparation of the apparatus.

The pressure detector, using the above described drip chamber 15, suffers from the following difficulty: In the drip chamber 15, sometimes the level of the liquid is abnormally raised for some reason, so that the liquid is caused to flow to the filter 19 provided for preventing the flow of liquid to the pressure sensor 18. However, if the filter 19 is wet, the flow of air is blocked and, as a result of which the pressure detector does not work. This failure greatly affects the functions of other parts of the blood processing apparatus, breaking down the blood processing apparatus, itself, and the medical treatment must be suspended. This is a serious problem and concerns the life of the patient.

SUMMARY OF THE INVENTION

It is an object of this invention to eliminate the above-described difficulties accompanying a conventional pressure detector. More specifically, an object of the invention is to provide a pressure detector which is disposable and low in manufacturing cost, and yet able to detect pressure variations with high accuracy and proficiency.

To solve the above-described problems, the invention provides a pillow type pressure detector which, according to the invention, comprises: a base board on the front surface of which a load cell type load sensor is mounted; a holder cover which is so provided as to be spaced a predetermined distance from the base board; a flat-plate-shaped load transmitting board and a flat-plate-shaped retaining board, arranged between the base board and the holder cover; a pillow type pressure reaction jig, between the load transmitting board and the retaining board; and, a pillow holding member which clamps predetermined portions of the pressure reaction jig provided over the base board and the holder cover.

The pressure detector may further comprise at least one mechanism for swinging the load transmitting board and the retaining board relative to each other, a mechanism elastically supporting the pillow holding member on the side of the base board, and a thin-plate-shaped depressing member, provided over the surface of the load, sensor to fixedly secure the load sensor to the base.

The pillow type pressure reaction jig is lower in manufacturing cost than the drip chamber. In the pressure detector of the invention, the pressure reaction jig is arranged between the base board, having the load cell type load sensor, and the holder cover. In setting the pressure reaction jig, the load transmitting board and the retaining board are operated in association with each other so that the pressure reaction jig may not be irregularly deformed. The load sensor is clamped from both side. The mechanism for elastically supporting the pillow holding member may be provided on the side of the base board. In order to prevent the load cell type load sensor from being irregularly deformed, the load sensor may be mounted on the base board with the aid of the thin-plate-shaped depressing member. That is, in the pressure detector of the invention, the factors in distortion attributing to the setting of the pressure detecting element are eliminated, with a result that the detection is improved in accuracy.

Thus, the pillow type pressure reaction jig can react to the internal pressure without changing its posture, thus transmitting variations in internal pressure to the load cell type load sensor accurately.

DETAILED DESCRIPTION OF THE PREFERRED EMBODIMENTS

This invention will be described with reference to its preferred embodiments shown in the accompanying drawings. The basic construction of the present invention will be described referring to FIGS. 14 and 15, illustrating a pillow type pressure detector constituting a first embodiment of the present invention.

Figure 14:
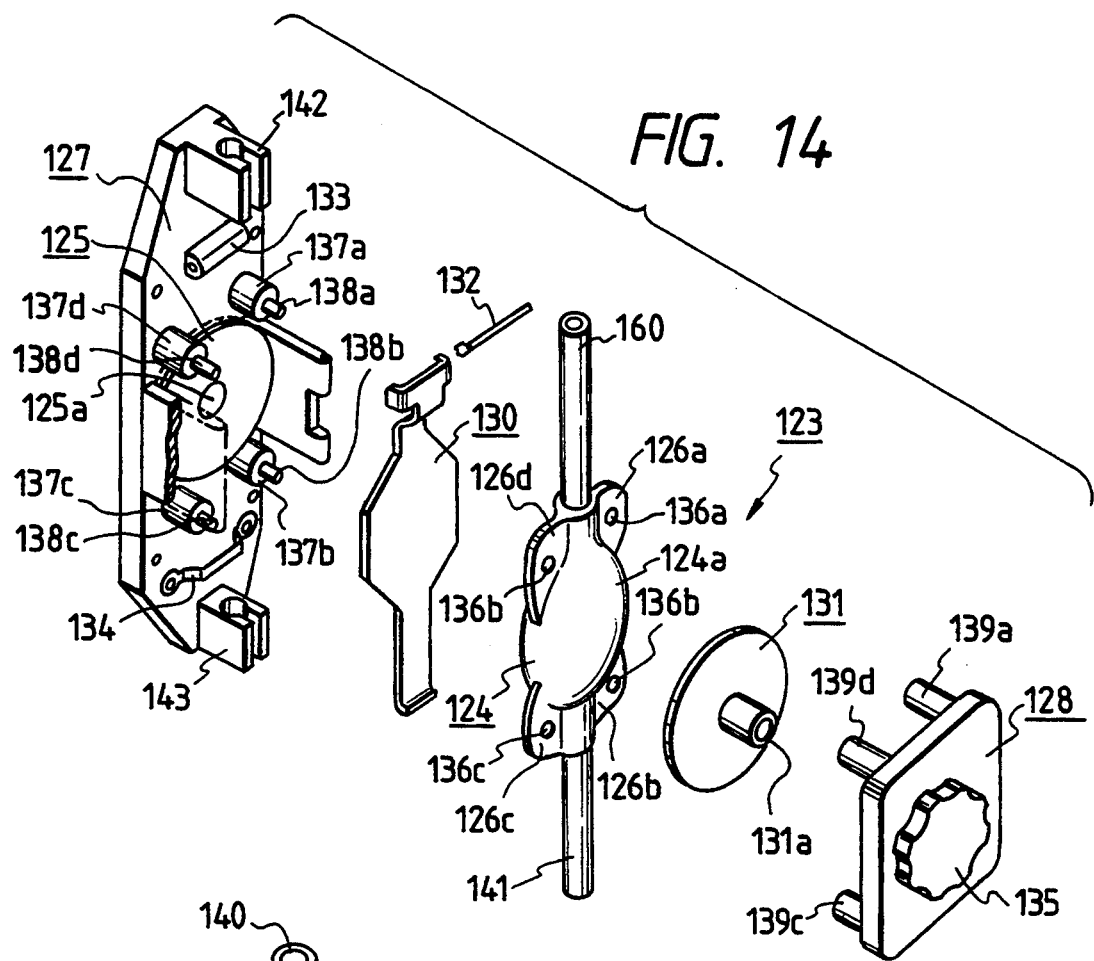
FIG. 14 is an exploded perspective view showing a pillow type pressure detector according to a further embodiment of the present invention.
Figure 15:
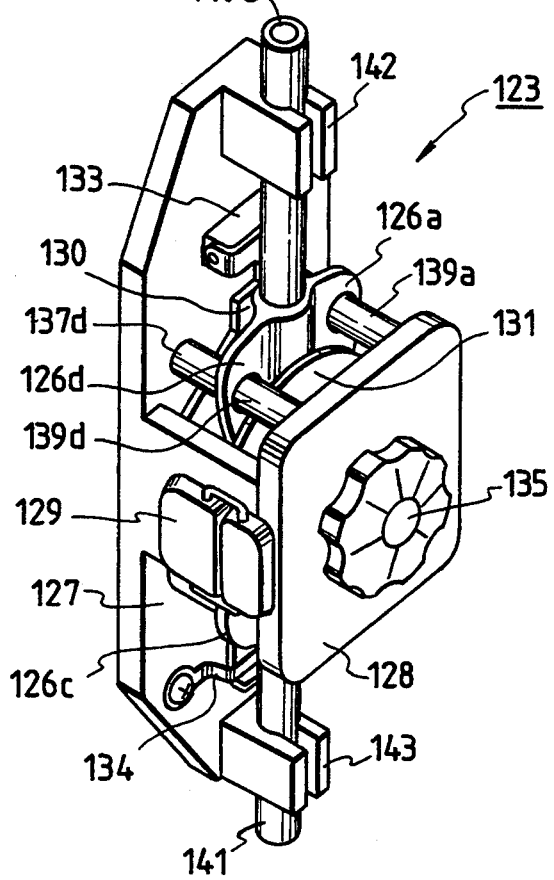
FIG. 15 is a perspective view showing the pillow type pressure detector of the embodiment of FIG. 14, as assembled.

In the embodiment of FIGS. 14 and 15, a pillow type reaction jig 124 and a load cell type load sensor 125 are utilized for detecting the pressure of the pressure detector 123. The pillow type pressure reaction jig 124 is in the form of a bag 124a formed by molding elastic material, such as, vinyl chloride. The jig bag 124a is normally elliptic in section but is inflated circular in section as the pressure increases. More specifically, the pressure reaction jig 124 includes a bag 124a which has four flat-plate-shaped ears 126a through 126d at its four corners. The load cell type load sensor 125 is commercially available and includes a load cell, distorted by a load applied thereto, to change its internal resistance. Therefore, by detecting the variation of the electrical output of the load cell, the value of the load is accurately detected.

In such pillow type pressure detector 123, the load cell type load sensor 125 is set on a front side of a base board 127. A holder cover 128 is mounted and retained to the base board 127 so as to be confronted with the base board 127 by a buckle 129 with a predetermined gap between holder cover 128 and base board 127. A flat-plate-shaped load transmitting board 130 and a flat-plate-shaped retaining board 131 are interposed between base board 127 and the holder cover 128.

Load transmitting board 130 is supported on base board 127 in a cantilever manner, that is, the base end of the load transmission board 130 is pivotally hinged to an axial support 133 of the base board 127 through a pin 132. The lower end of load transmission board 130 is retained in place by a leaf-spring 134 so that the load transmission board 130 is spaced from base board 127 a constant distance. Sensing portion 125a of load cell type load sensor 125 is in contact with a surface of a base plate side of the load transmission board 130.

The retaining board 131 has a threading portion 131a which is threadingly engaged with an operation handle 135 so that the retaining board 131 can be adjustably moved toward and away from holder cover 128.

Pillow type pressure reaction jig 124 is disposed and held between boards 130 and 131 in such a manner than small holes 136a–136d, provided in the ears 126a–126d are supportingly received on projections 138a–138d of hold pins 137a–137d implanted on the base board 127 with the projections 138a–138d being received in pin caps 139a–139d of the holder cover 128, respectively. Hold pins 137a–139d and pin cap 139a–139d serves as a pillow holding member for mounting pressure reaction jig 124 between load transmission board 130 and the retaining board 131 and securely clamping the ears 126a–126d of the pressure reaction jig 124 when the buckle 129 is closed.

Pillow type pressure reaction jig 124 is connected to a fluid flow-in pipe 140 and a fluid flow-out pipe 141. The base board 127 has tube holders 142 and 143 for holding fluid flow-in pipe 140 and fluid flow-out pipe 141, respectively.

The pillow type pressure detector, thus constructed, has the following advantages: The pressure detector is formed by combining the pillow type pressure reaction jig and the load cell type load sensor, which are low in manufacturing cost and have been used in the art, with the particular holder mechanism. The pressure detector thus formed is high both in accuracy and in reliability, and low in manufacturing cost and, accordingly, disposable. Hence, in the case where the pressure detector of the invention is applied to a medical instrument, such as, a blood processing apparatus, the preparatory time is much shorter than in the case where the conventional blood processing apparatus is employed. In addition, the pressure detector is substantially free from failure or erroneous operation, thus eliminating the forcible suspension of medical treatment.

However, because the pressure detector is not always satisfactory as a means for detecting pressure variations with high accuracy, the following modified embodiments are further provided.

Figure 3:
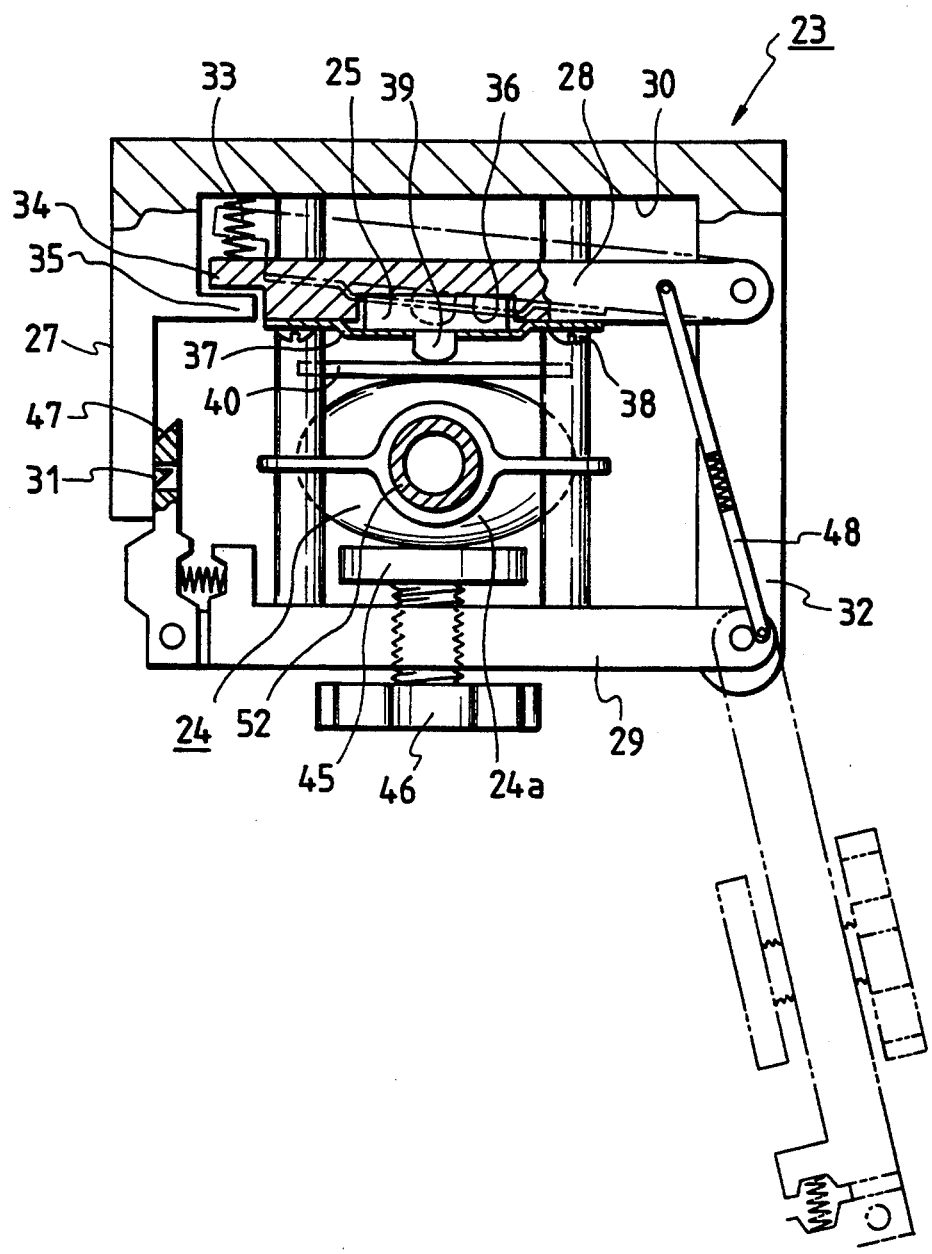
FIG. 3 is a plan view, partly in section, of the pressure detector of FIGS. 1 and 2, with the cover closed in solid lines and open in broken lines.

A shown in FIGS. 1 through 8, a pillow type pressure detector 23, constitutes a second embodiment of the invention. In this second embodiment, a pillow type reaction jig 24 and a load cell type load sensor 25, FIG. 3, are utilized for detection of the pressure of the pressure detector 23, FIG. 1. The pillow type pressure reaction jig 24 is in the form of a bag formed by molding elastic material, such as, vinyl chloride. The jig 24 is normally elliptic in section but is inflated circular in section as the pressure increases. More specifically, the pressure reaction jig 24 includes a bag 24a which has four flat-plate-shaped ears 26a through 26d at four corners. The load cell type load sensor 25 is commercially available, and it is designed so that the load cell is distorted by a load applied thereto to change the internal resistance. Therefore, by detecting the variation of the electrical output of the load cell, the value of the load can be detected accurately.

The pillow type pressor detector 23 comprises: a mounting stand 27; a base board 28 supported on the front side of mounting stand 27 in such a manner so that it is swingable horizontally (or vertically in FIG. 3); and a holder cover 29 supported in such a manner so that it is spaced a predetermined distance from the base board 28.

The mounting stand 27 has a recess 30, FIG. 3, in its bottom wall, and a protrusion 31 on its one side wall extended from its one side which is used to lock the holder cover 29, and supports 32 extended from the opposite side in such a manner as to confront with the aforementioned one side wall. The base board 28 is swingably supported through its one side on the base end portions of the supports 32, while the holder cover 29 is also swingably supported through its one side on the top end portions of the supports 32. The mounting stand 27 has tube holders 54 and 55 on the front surface at the upper and lower edges for holding a fluid flow-in pipe 52 and a fluid flow-out pipe 53, respectively. Those pipes are connected to the pillow type pressure reaction jig 24. Hold pins 50a through 50d are embedded in the central portion of the front surface of the mounting stand 27 and are inserted into small holes formed in the four ears 26a through 26d of the pillow type pressure reaction jig 24, respectively.

The base board 28 is set swingably back and forth with the aid of a spring 33, FIG. 3, set in the recess 30 of the mounting stand 27. The base board 28 has a stopper 34, which is normally pushed against the protrusion 35 of the mounting stand 27. The base board 28 has a chamber 36 formed in the central portion of the front surface, in which the aforementioned load cell type load sensor 25 is set. In order that the load sensor may not play or may not be set unstable, the inner surface (especially the bottom surface) is finished with high precision. In order to prevent the load sensor 25 fitted in the chamber 36 from being raised from the latter 36, a retaining member 37 such as a stainless plate 0.1 mm in thickness is set over the load sensor 25 with screws 38.

Figure 4:
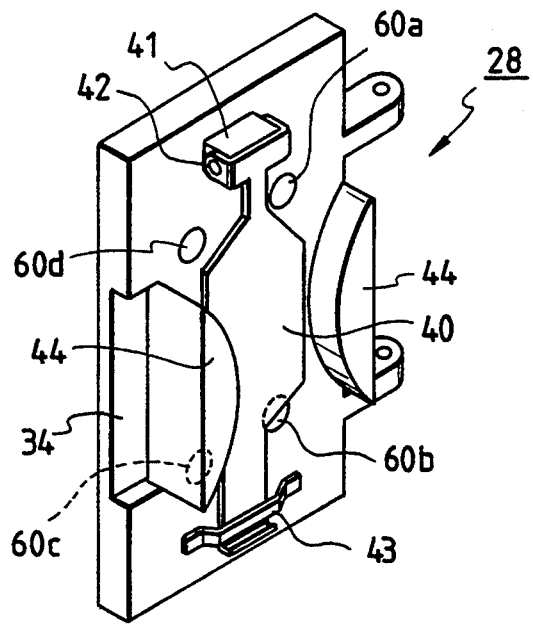
FIG. 4 is a perspective view of a base board in the pressure detector of the embodiment of FIGS. 1-3.

A load transmitting board 40 is swingably mounted on the base board 28 so that it is brought into contact with the sensing protrusion 39 of the load sensor 25. More specifically, as shown in FIG. 4, the base end portion of the load transmitting board 40 is coupled through a pin 42 to an engaging protrusion 41 formed on the base board 28; that is, it is cantilevered. The tip end portion of the load transmitting board 40 is held by a leaf spring 43 so that it is held spaced a predetermined distance from the base board 28. Side walls 44 and 44 are provided on both sides of the load transmitting board 40 of the base board 28 so that a predetermined gap is held between the base board 28 and the pillow type pressure reaction jig. 24, FIG. 1. The side walls 44 and 44 are used to guide the installation of the pressure reaction jig 24, and therefore may be eliminated. The base board 28, FIG. 4, has though-holes 60a through 60d around the load transmitting board 40 into which the hold pins 50a through 50d, FIG. 5, embedded in the mounting stand 27 are inserted, respectively.

Figure 5:
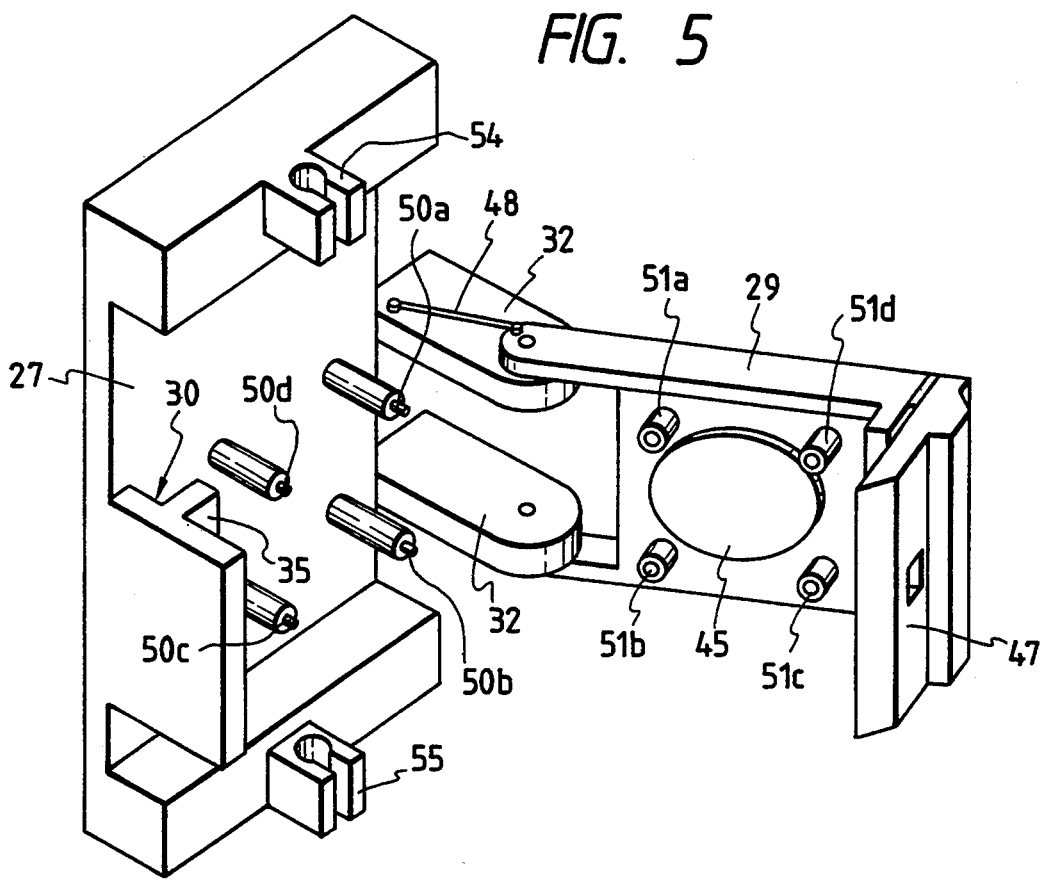
FIG. 5 is a perspective view of the mounting stand and the holder cover in the pressure detector of the embodiments of FIGS. 1-3, with the cover open.
Figure 6:
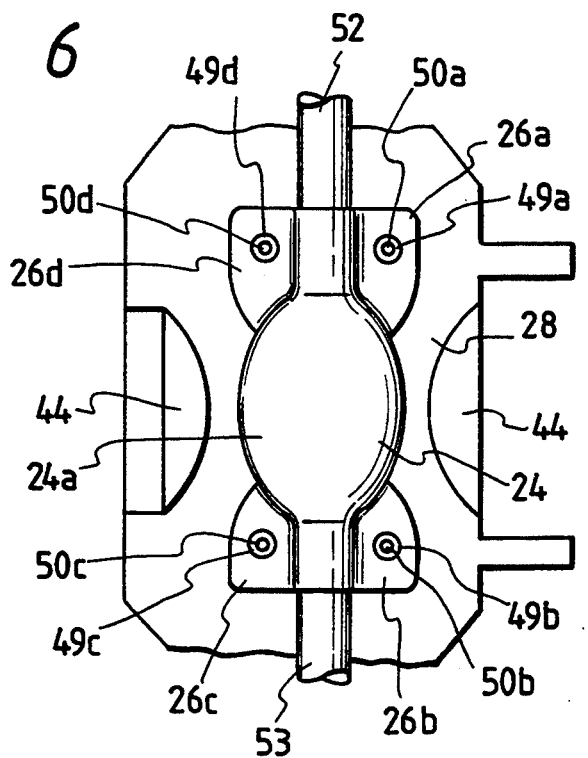
FIG. 6 is a front view showing the base board and a pressure reaction jig in the pressure detector of the embodiment of FIGS. 1-3.
Figure 7:
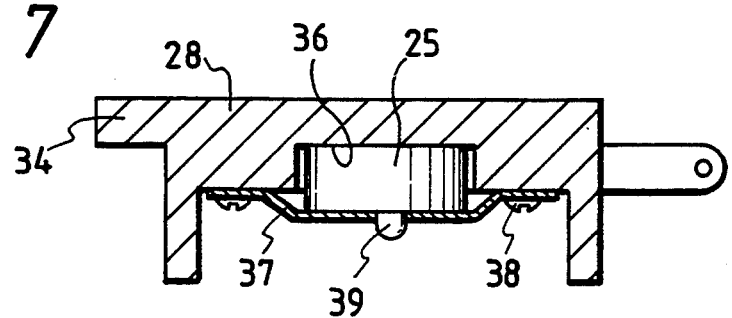
FIG. 7 is a cross sectional view of the base board of the pressure detector of FIG. 6.
Figure 8:
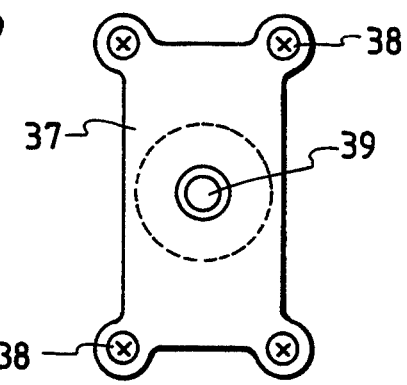
FIG. 8 is a front view showing a part of the base board of the pressure detector of FIGS. 6 and 7.

The holder cover 29, FIG. 5, has a flat-plate-shaped retaining board 45 mounted over its inner surface which is confronted with the base board 28, in such a manner that the retaining board 45 is aligned with the load transmitting board 40. More specifically, the retaining board 45 is mounted on the shaft of an operating handle 46, FIG. 2, threadably engaged with the holder cover 29, so that the retaining board is threadably moved to or from the holder cover by turning the operating handle 46. The holder cover 29 has a pawl 47 at its side which is opposite to the pivoting side. The pawl 47 is engaged with the locking protrusion 31, FIG. 3 on the mounting stand 27. The pawl 47 may have elastic property for the engagement, or otherwise, may be arranged such that, as best shown in FIG. 3, a ridged pawl 47' is pivotally supported onto the holder cover 29 and biased by a spring interposed therebetween.

The base board 28 and the holder cover 29, FIG. 3, are swingably coupled through their arms to the supports 32 of the mounting stand 27, and the arms are coupled to each other through a rod 48.

The pillow type pressure reaction jig 24 is disposed between the load transmitting board 40 and the retaining board 45. With the pillow type pressure reaction jib 24 interposed between the boards 40 and 45, small holes 49a through 49d, FIG. 6, formed in the ears 26a through 26d are engaged with the hold pins 50a through 50d, FIG. 5, inserted into the through-holes 60a through 60d of the base board 28, respectively. Under this condition, the hold pins 50a through 50d are fitted in pin caps 51a through 51d of the holder cover 29, respectively. Hence, when, with the pressure reaction jig 24 held between the load transmitting board 40 and the retaining board 45, the pawl 47 is engaged with the locking protrusion 31, the hold pins 50a through 50d and the pin caps 51a through 51d act to clamp the ears 26a through 26d of the pressure reaction jig 24; that is, they serve as a pillow holding member.

The operation of the pillow type pressure detector 23 thus constructed will be described.

Figure 1:
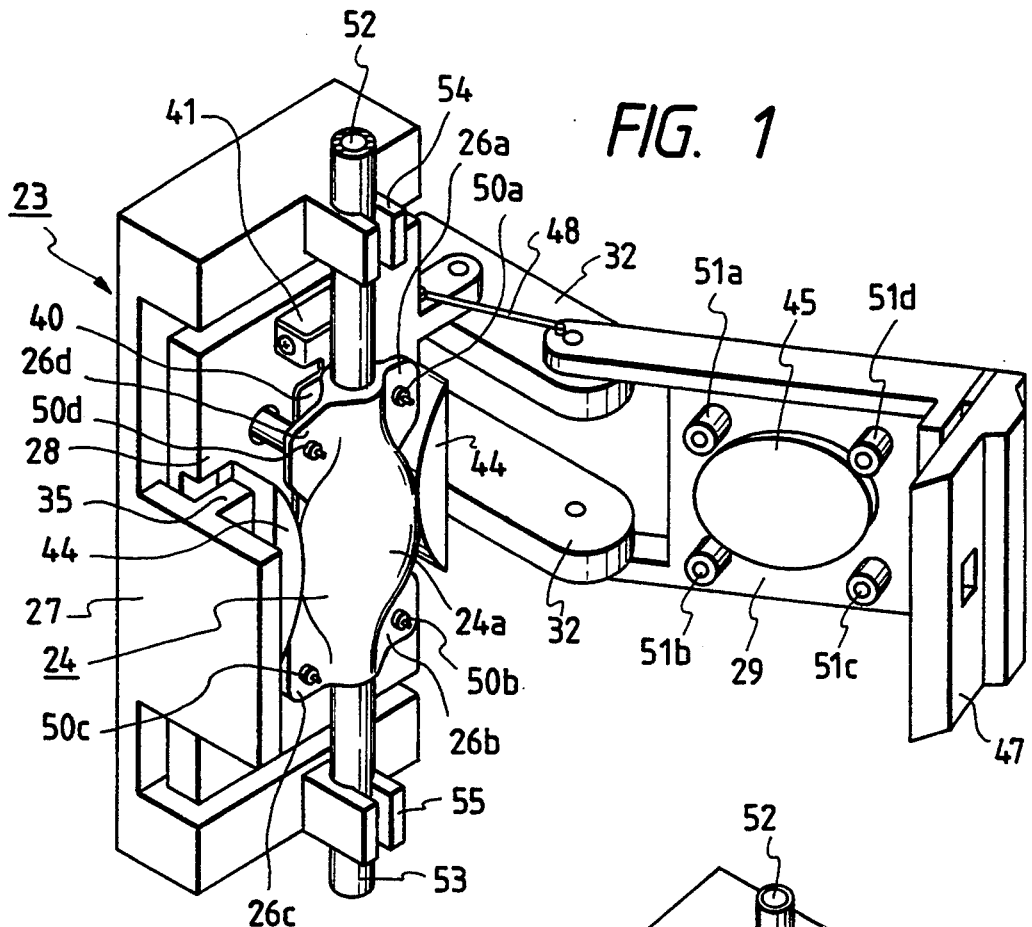
FIG. 1 is a perspective view of a pressure detector of one embodiment of the invention, with the holder cover opened.
Figure 2:
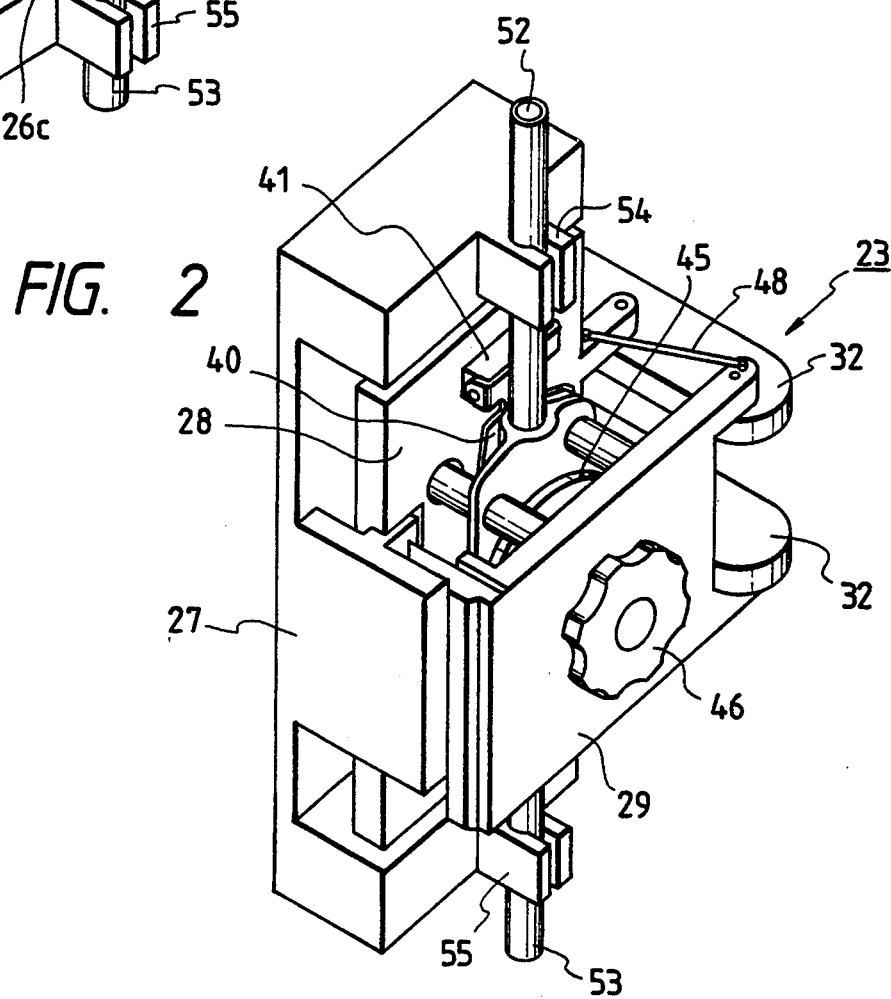
FIG. 2 is a perspective view of the pressure detector of FIG. 1, with the holder cover closed.

First, the pillow type pressure reaction jig 24 is set with the holder cover 29 opened as shown in FIG. 1 and 5. The holder cover 29 is coupled through the rod 48 to the base board 28, as was described above. Hence, with the holder cover 29 opened, the base board 28 is retracted towards the bottom of the recess 30 of the mounting stand 27 against the elastic force of the spring 33 as indicated by the chain lines in FIG. 3.

In the embodiment, the pillow type pressure reaction jib 24 is set by inserting the hold pins 50a through 50d protruded through the base board 28 into the small holes 49a through 49d of the ears 26a through 26d of the pressure reaction jig, in the space between the base board 28 retracted and the holder cover 29 opened. The liquid flow-in pipe 52 and the liquid flow-out pipe 53 are fixedly fitted in the tube holders 54 and 55 of the mounting stand 27, respectively. In this case, the hold pins 50a through 50d and the tube holders 54 and 55 are in one and the same plane. Therefore, the liquid flow-in pipe 52 and the liquid flow-out pipe 53 can be set straight in alignment with the bag 24a.

In this setting operation, the load transmitting board 40 has been retracted towards the bottom of the recess 30 of the mounting stand as indicated by the broken lines in FIG. 3, and the bag 24a of the pressure reaction jig 24 will not be brought into direct contact with the load transmitting board 40. This eliminates the following difficulty: If the pressure detector is of the type that the base board 28 is fixedly secured to the mounting stand 27, the ears 26a, through 26d of the pressure reaction jig 24 may be pulled. Therefore, when the small holes 49a through 49d are engaged with the pin caps 51a through 51d, the bag 24a may be brought into contact with the load transmitting board 40; that is, the pressure reaction jig 24 may be set with the bag 24a deformed.

At the start of the jig setting operation, the pressure reaction jig 24 is positioned as indicated by the solid lines in FIG. 3; that is, its position is the same as that of the pressure reaction jig 24 which has been set. Thus, the pressure reaction jig 24 will not be moved so much until it has been set.

Figure 12:
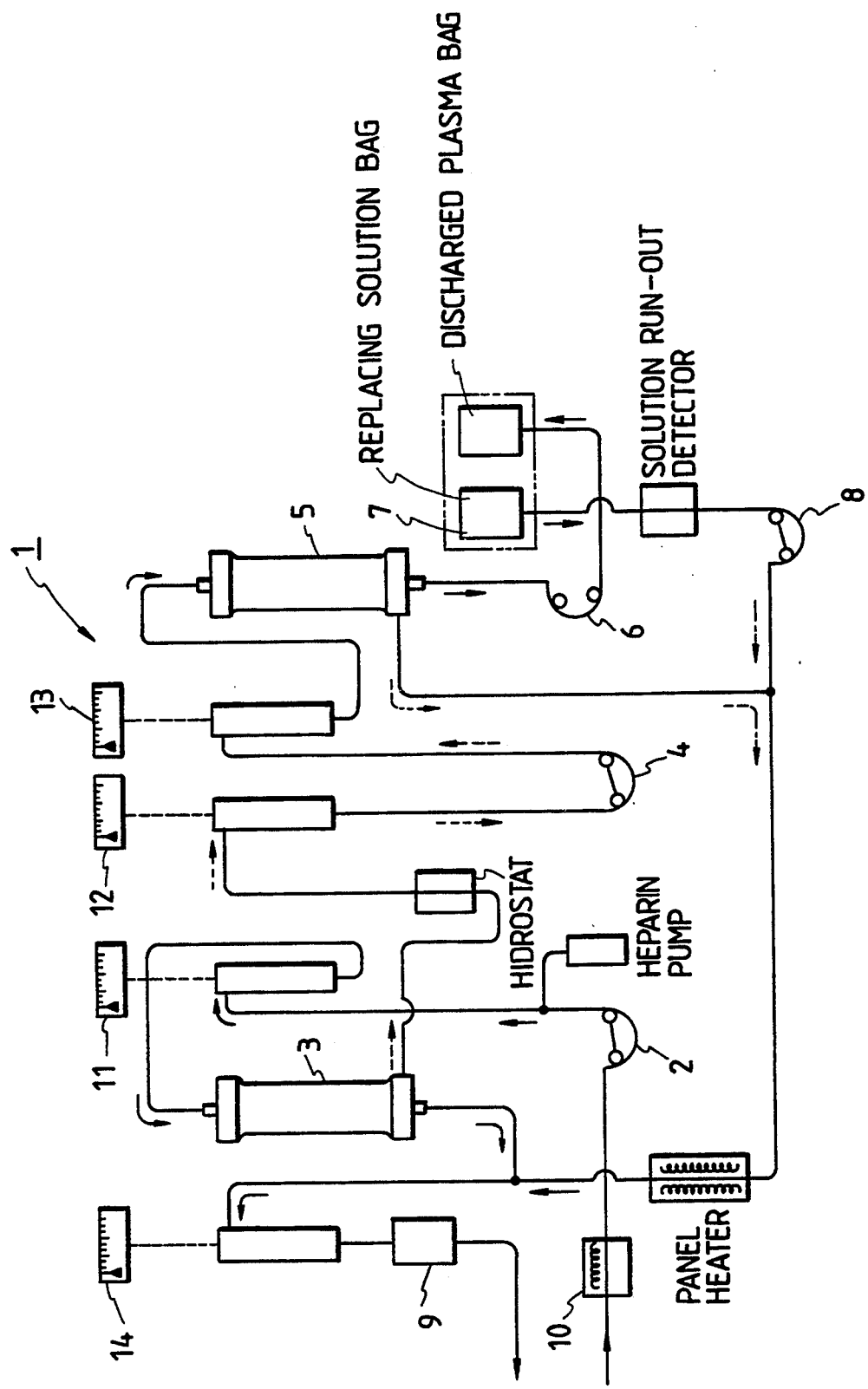
FIG. 12 is a block diagram of the arrangement of a conventional blood processing apparatus.

This will be described in more detail. In the case where the blood processing apparatus as shown in FIG. 12 is mounted on one board, and the pressure detector of the invention is combined with it, the aforementioned mounting stand 27 is fixedly mounted on the board of the blood processing apparatus 1, and therefore the pipes of the blood pump 2, the filter 3, etc. mounted on the board, the fluid flow-in pipe 52 and the fluid flow-out pipe 53 of the pressure reaction jig 24, and the bag 24a of the latter 24 can be arranged in one and the same plane. Hence, for instance in replacing the pressure reaction jig 24, those pipes 52 and 53 will never be bent; that is, the piping of the apparatus is increased in service life.

After the pressure reaction jig 24 has been set in the above-described manner, the holder cover 29 is swung from its position indicated by the broken lines to the position indicated by the solid lines in FIG. 3 until the elastic pawl 47 is engaged with the locking protrusion 31 on the mounting stand 27; that is, the holder cover 29 is closed. In association with the closure of the holder cover 29, the base board 28 is also swung with the aid of the rod 48; that is, it is returned to the position indicated by the solid line in FIG. 3. As the holder cover 29 is closed, causing the base board 28 to return in the above-described manner, the hold pins 50a through 50d inserted into the small holes 49a through 49d of the ears 26a through 26d of the pressure reaction jig 24 are fitted in the pin caps 51a through 51d of the holder cover 29, respectively, so that the pressure reaction jig 24 is clamped through the ears 26a through 26d from both sides.

In addition, as the holder cover 29 is closed, the load transmitting board 40, on the base board 28, and the retaining board 45 of the holder cover 29, clamp the bag 24a of the pressure reaction jig 24 from both sides at the same time. Hence, members 40 and 45, when set, do not twist the bag 24.

Thus, the operation of setting the pressure reaction jig 24 has been accomplished. However, the output of the load sensor 25 is not always correct depending on how the pressure reaction jig 24 is set. Hence, it is necessary to calibrate a detection value outputted by the load sensor 25; that is, it is necessary to set an initial value for the load sensor 25. This initial value setting operation is carried out as follows: That is, the operating handle 46 of the holder cover 29 is turned to move the retaining board 45 to or from the holder cover 29, thereby to adjust the force of pushing the bag 24a of the pressure reaction jig 24. That is, the force applied to the load sensor 25 through the load transmitting board 40 is changed. Thus, the magnitude (initial value) of the signal which the load sensor 25 outputs when no fluid is supplied to the pressure reaction jig 24, that is, when the latter 24 is not in use, is set. By setting the initial value, the gradient of the output signal characteristic curve of the pressure reaction jig 24 is determined.

After the initial value of the load sensor has been set, in the above-described manner, a fluid under test, such as blood, is allowed to flow in the pressure reaction jig 24 through the fluid flow-in pipe 52 and to flow out of it through the fluid flow-out pipe 53. In this operation, in the load sensor 25, the load cell reacts to the pressure of the fluid in the pressure reaction jig 24, thus continuously detect the pressure of the fluid. A computer built in the detector automatically calculates the output of the load sensor 25 according to the gradient of the characteristic curve with the initial value set, and indicates such calculation as a detected fluid pressure.

With the pillow type pressure detector 23 applied to the blood processing apparatus 1 shown in FIG. 12, the upper and lower limit values of each of the blood collection pressure, blood filtration pressure, plasma pressure, plasma filtration pressure, and reinfusion pressure, and the values between the upper and lower limit values can be detected with high accuracy. Thus, the pillow type pressure detector 23 of the invention is excellent as means for controlling medical instruments. In addition, it can be installed on the conventional blood processing apparatus readily and quickly, which means that the preparatory time can be greatly reduced. Furthermore, the pressure detector 23, unlike the conventional drip chamber 15, is free from the difficulty that the filter 19 is wetted, and the apparatus becomes out of order, as a result of which the medical treatment must be suspended.

When another patient comes, a disposable blood circuit which is newly installed on the blood processing apparatus 1 is washed and primed. In this case, the pillow type pressure reaction jig 24 included in the disposable blood circuit is a new one, and therefore the initial value of the load sensor 25 must be set. This can be readily achieved merely by turning the operating handle 46. The above-described pressure reaction jig 24 has been actually employed as one of the limit switches for detecting only the upper or lower limits of pressures.

If the pressure reaction jig 24 is merely combined with the load sensor 25, then its bag 24a may be abnormally deformed. In this case, it is impossible to detect pressures accurately. In the embodiment, in order to continuously detect fluid pressures with high accuracy, the pressure reaction jig 24 is held as follows:

The pressure reaction jig 24 and the load sensor 25 are so set that they are free from distortion.

As for the load sensor 25, the inner surface of the chamber 36, formed in the base board 28, is finished with high precision so that the load sensor 25 may not play in the chamber 36. In addition, in order to prevent the load sensor 25 from coming off the chamber 36, for instance when the pressure reaction jig 24 is replaced, the thin-plate-shaped retaining member 37 is provided.

On the other hand, as for the pressure reaction jig 24, predetermined gaps are provided between the bag 24a and the side walls 44 and 44 so that, when the bag 24a inflates with sensing pressure, it may not be irregularly deformed by the side walls 44 and 44. If it is irregularly deformed, the pressure applied to the bag 24 is imbalanced, so that it is not correctly transmitted to the load transmitting board 40. Furthermore, as was described before, in order to eliminate the difficulty that the pressure reaction jig 24 is deformed when set, the base board 28 and the holder cover 29 are operated (opened and closed) in association with each other, to clamp the pressure reaction jig 24 from both sides at the same time.

In the pressure detector 23 of the invention, the pressure reaction jig 24 is held set with special means, so that the pressure detecting operation can be achieved stably and free from distortions. That is, the ears 26a through 26d of the pressure reaction jig 24 are fixedly held with the base board 28 and the holder cover 29 so that the bag 24a inflates regularly and stably while sensing the fluid pressure. The inflation of the bag, due to the fluid pressure is transmitted, through the load transmitting board 40, to the load sensor 25. The base end portion of the load transmitting board 40 is pivotally supported with the pin 42, so that transmitting board 40 is prevented from being twisted. Thus, the load is transmitted accurately.

Figure 9:
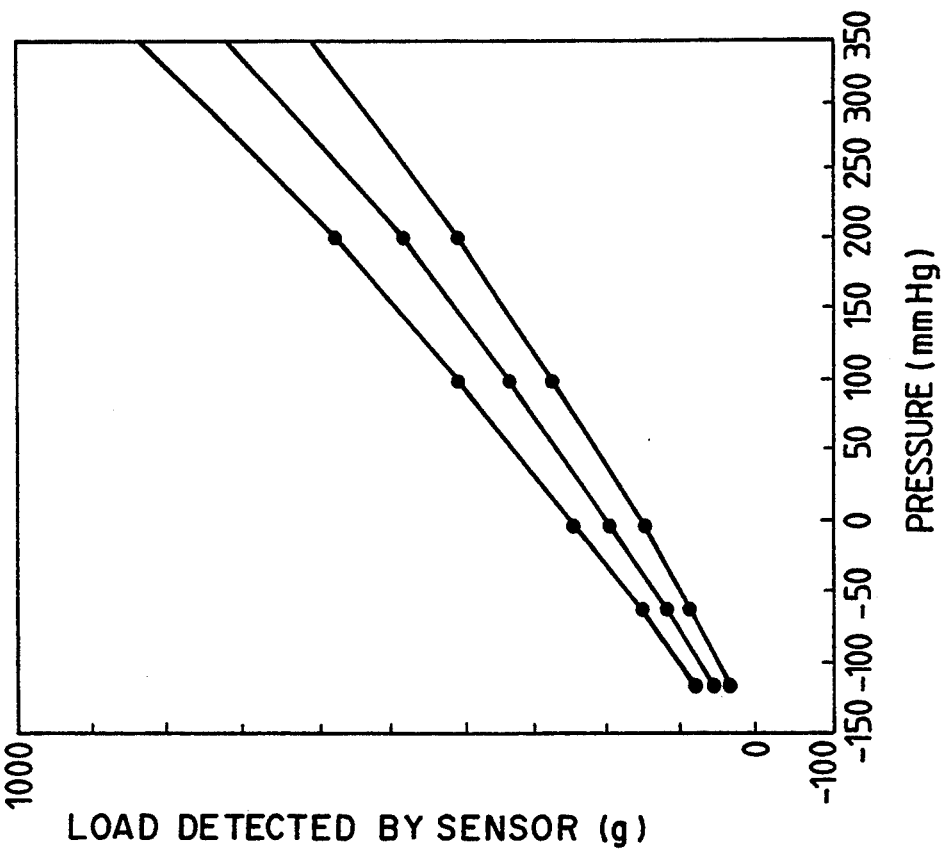
FIG. 9 is a graphic representation indicating the results of measurements performed with the pressure detector of FIGS. 1-3.

FIG. 9 shows the results of experiments in which fluid pressures were measured with the pillow type pressure detector 23 according to the first embodiment of the invention. In the experiments, the distance between the holder cover 29 and the retaining board 45 was changed to provide three different initial values. In each of the experiments, the fluid pressure was gradually increased, and then decreased to the original value. This method can detect the hysteresis in the output of the pressure detector 23. In each of the experiments, as shown in FIG. 9, the values detected by the load cell type load sensor 25, with respect to the fluid pressures, formed a quadratic curve, and the fluid pressures were detected accurately with no hysteresis. By changing the distance between the holder cover 29 and the retaining board 45 with the operating handle, the initial value of the load sensor 25 can be changed: that is, the gradient of the output signal characteristic of the load sensor 25 can be determined.

Figure 10:
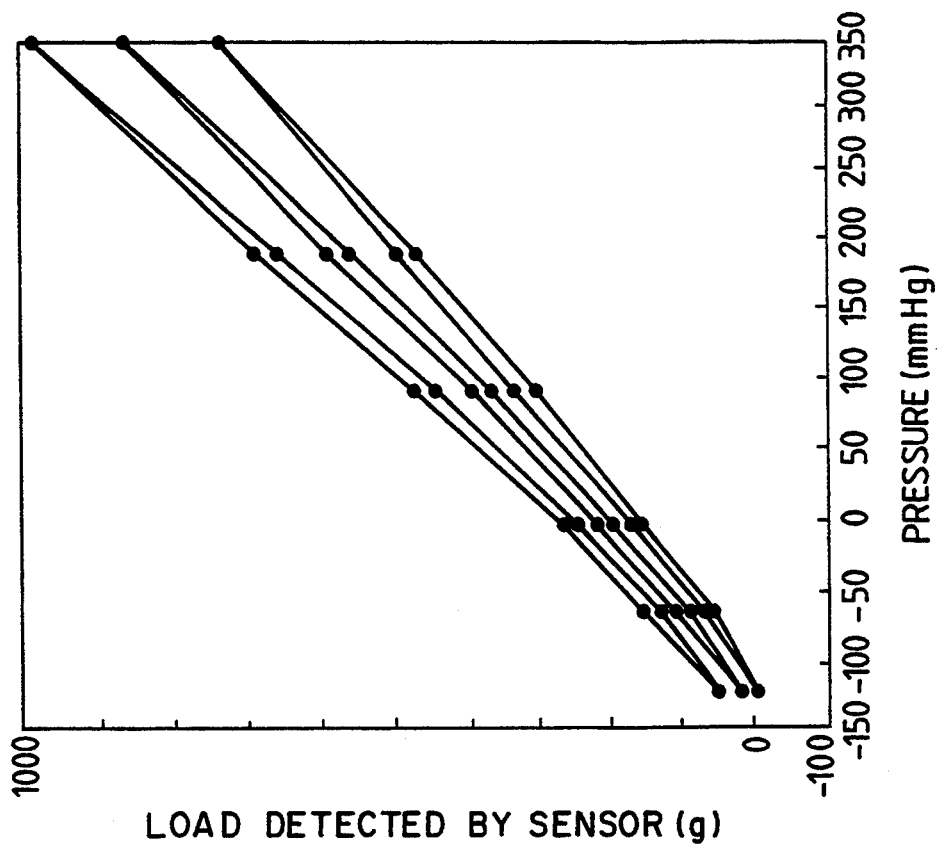
FIG. 10 is also a graphic representation of a hysteresis which may occur with the pressure detector.

For reference only, FIG. 10 shows the results of experiments in which fluid pressures were detected with the load sensor 25 and the pressure reaction jig 24 set twisted intentionally. In each of the experiments, the curve formed when the pressure was increased was different from that which was formed when the pressure thus increased was decreased; that is, a hysteresis was formed. This means that it is important to set the load sensor 25 and the pressure reaction jig 24 correct in posture.

Figure 11:
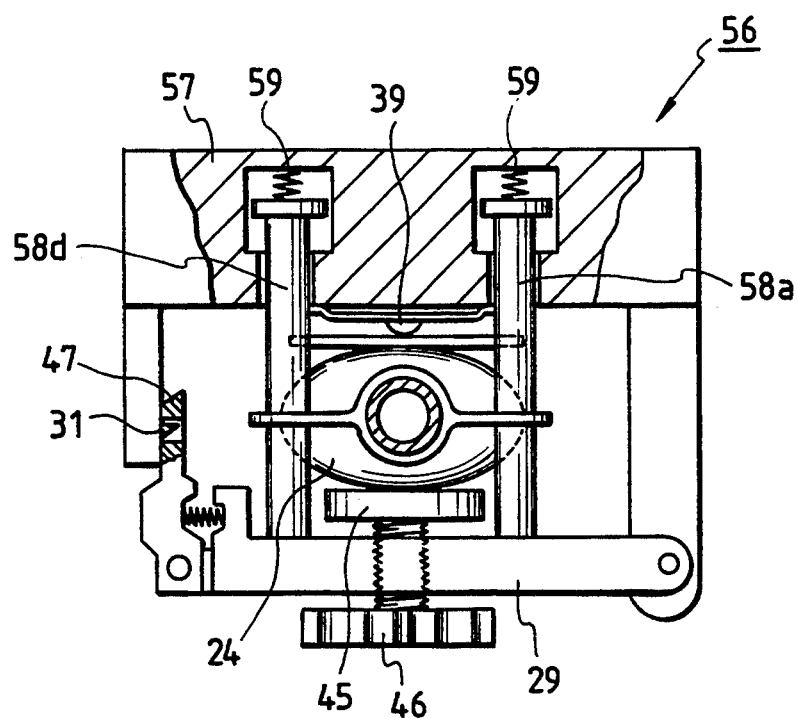
FIG. 11 is a plan view, partly in section, showing another embodiment of the pressure detector of the invention.
Figure 13:
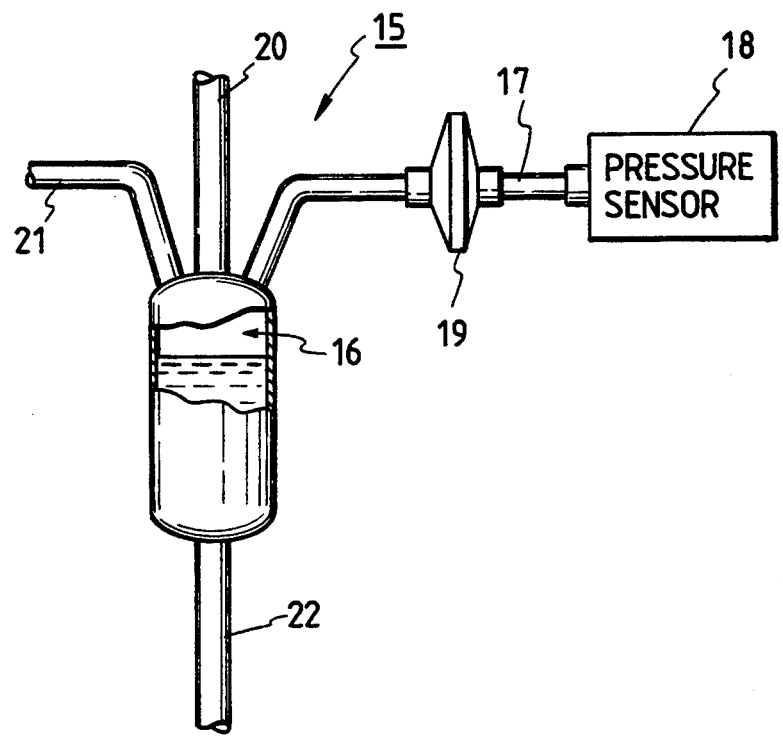
FIG. 13 is a front view of a drip chamber in the conventional blood processing apparatus.

FIG. 11 shows another pillow type pressure detector 56, which constitutes a second embodiment of the invention. In the second embodiment, hold pins 58a through 58d of a base board 57, supporting the ears 26a through 26d of the pressure reaction jig 24, are elastically supported by springs 59 in the base board 57. The base board 57 is stationary. One end portion of the holder cover 29 is coupled to the base board so that the holder cover 29 is swingable (opened and closed). The pressure reaction jig 24 can be set as follows: That is, with the pressure reaction jig 24 placed on the hold pins 58a through 58d, the holder cover 29 is closed. In this case, too, the pressure reaction jig 24 can be set in its natural posture, with the ears 26a through 26d being not pulled. Hence, the pressure detecting operation is free from the formation of the hysteresis. The other arrangements, operations and effects are fundamentally the same as those of the first embodiment.

While a few embodiments of the invention has been described, it should be noted that the invention is not limited thereto or thereby. For instance, the configuration and dimension of the base board 28 or 57 and the holder cover 29, and the configuration and number of the ears 26a through 26d of the pressure reaction jig 24 may be changed as the case may be. In addition, the means for holding the ears 26a through 26d may be replaced by holding means such as clipping means or clamping means. The pressure detector 23 may be applied to medical instruments, other than the blood processing apparatus 1, and other fluid pressure detecting instruments.

As was described above, the pressure detector is formed by combining the pillow type pressure reaction jig and the load cell type load sensor, which are low in manufacturing cost and have been actually used in the art, by using the particular holder mechanism, according to the invention. The pressure detector, thus formed, is high both in accuracy and in reliability, and low in manufacturing cost and, accordingly, disposable. Hence, in the case where the pressure detector of the invention is applied to a medical instrument, such as, a blood processing apparatus, the preparatory time is much shorter than in the case where the conventional one is employed. In addition, the pressure detector is substantially free from failure or erroneous operation, which eliminates the forcible suspension of the medical treatment. Furthermore, the load cell type load sensor and the pressure reaction jig can be set and held correct in posture so that they may not suffer from irregular distortion. Hence, no hysteresis occurs with the pressure detection value of the pressure detector of the invention.

What is claimed is:

1. A pillow type pressure detector, comprising:
   a base board on the front surface of which a load cell type load sensor is mounted;
   a holder cover having means for spacing said holder cover a predetermined distance from said base board;
   a flat-plate-shaped load transmitting board and a flat-plate-shaped retaining board positioned between said base board and said holder cover;
   a pillow type pressure reaction jig positioned between said load transmitting board and said retaining board, said pillow type pressure reaction jig including a bag capable of having a pressure medium supplied therein; and a pillow holding member for clamping predetermined portions of said pressure reaction jig over said base board and said holder cover.

2. The pressure detector according to claim 1, further comprising:

means for simultaneously pivoting said load transmitting board and said retaining board relative to said base board.

3. The pressure detector according to 1, further comprising:

means elastically supporting said pillow holding member on the side of said base board.

4. The pressure detector according to claim 1, further comprising:

a thin-plate-shaped depressing member provided over the surface of said load sensor for fixedly secure said load sensor to said base.

* * * * *